United States Patent [19]

Abe

[11] Patent Number: 4,493,824
[45] Date of Patent: Jan. 15, 1985

[54] HAIR RINSE COMPOSITION

[75] Inventor: Yoshiaki Abe, Tokyo, Japan

[73] Assignee: Kao Soap Co., Ltd., Tokyo, Japan

[21] Appl. No.: 405,280

[22] Filed: Aug. 4, 1982

Related U.S. Application Data

[63] Continuation of Ser. No. 200,399, Oct. 24, 1980, abandoned.

[30] Foreign Application Priority Data

Jan. 9, 1980 [JP] Japan .................................. 55-1112

[51] Int. Cl.$^3$ .......................... A45D 7/00; A61K 7/06; A61K 7/08
[52] U.S. Cl. ........................................... 424/70; 132/7
[58] Field of Search ........................................... 424/70

[56] References Cited

U.S. PATENT DOCUMENTS

| | | | |
|---|---|---|---|
| 3,155,591 | 11/1964 | Hilfer | 424/70 |
| 4,001,394 | 1/1977 | Fogel et al. | 424/70 |
| 4,013,786 | 3/1977 | Cella et al. | 424/71 |
| 4,144,326 | 3/1979 | Luedicke, Jr. et al. | 424/70 |
| 4,160,823 | 7/1979 | Watanabe et al. | 424/71 |

FOREIGN PATENT DOCUMENTS

| | | | |
|---|---|---|---|
| 4639360 | 11/1971 | Japan | 424/70 |
| 4811951 | 4/1973 | Japan | 424/70 |
| 940188 | 10/1963 | United Kingdom | 424/70 |

OTHER PUBLICATIONS

Drug & Cosmetic Industry, 2/1966, vol. 98, No. 22, pp. 124 and 127.
Kluge, Amer. Perf. & Cosm. 3/1966, vol. 81, No. 3, pp. 35 to 38 and 40.

Primary Examiner—Dale R. Ore
Attorney, Agent, or Firm—Oblon, Fisher, Spivak, McClelland & Maier

[57] ABSTRACT

A hair rinse composition comprising one or more quaternary ammonium salts, a silicone derivative and a polyethylene glycol is disclosed. The ammonium salts are represented by

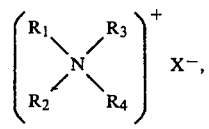

wherein one or two of the R's are certain higher alkyl or hydroxyalkyl groups and the rest are certain lower alkyl, lower hydroxylalkyl, benzyl or polyoxyethylene groups, and X is a halogen atom or alkylsulfuric group. The hair rinse composition according to this invention has superior rinsing effects, i.e., effectiveness to impart adequate softness, smoothness and antistatic property to hair.

1 Claim, No Drawings

HAIR RINSE COMPOSITION

This is a continuation of application Ser. No. 200,399, filed Oct. 24, 1980, now abandoned.

BACKGROUND OF THE INVENTION

1. Field of the Invention

The present invention relates to a hair rinse composition and particularly a hair rinse composition comprising a quaternary ammonium salt, a silicone derivative and a polyethylene glycol.

2. Description of the Prior Art

Hair rinse compositions containing a quaternary ammonium salt such as distearyldimethyl ammonium chloride have been used as an effective component to eliminate various inconveniences after shampooing.

Hair rinse compositions are intended to give the hair softness, smoothness and antistatic property. However, it is impossible to obtain adequate effectiveness for the softness and smoothness with use of such a quaternary ammonium salt. Accordingly, it has been a common practice to incorporate in conventional hair rinse compositions, fats and oils such as a higher alcohol, a glyceride or a liquid paraffin in order to improve on the above mentioned deficiency.

Heretofore, it has been believed that an emulsified dispersion system consisting of an appropriate fat and oil, and a quaternary ammonium salt is most preferable. However, the quaternary ammonium salt does not have the ability to emulsify and disperse a fat and oil in a sufficient amount to produce the effectiveness and in a stabilized condition. Accordingly, attempts have been made to incorporate a non-ionic surface active agent having a higher hydrophilic property thereby, to maintain the emulsified dispersion system in a stabilized condition. However, such non-ionic surface active agents having a higher hydrophilic property considerably reduce the rinsing effect. Accordingly, a hair rinse composition containing such a non-ionic surface active agent having a higher hydrophilic property does not provide a sufficient rinsing effect when a quaternary ammonium salt and fat and oil are incorporated thereto.

On the other hand, conventional hair rinse compositions do not have adequate rinsing effectiveness, i.e., effectiveness to impart softness, smoothness and antistatic properties to the hair. The development of an improved hair rinse composition has heretofore been desired.

SUMMARY OF THE INVENTION

The present inventors have conducted extensive research to eliminate the deficiencies of conventional hair rinse compositions and to obtain a hair rinse composition having a superior rinsing effect. As a result the present inventors have found that it is possible to overcome the above mentioned deficiencies and to obtain a hair rinse composition having a superior rinsing effect by incorporating into a hair rinse composition a combination of a quaternary ammonium salt with a silicone derivative and a polyethylene glycol. Thus, the present invention has been accomplished.

The present invention provides a hair rinse composition comprising the following three components:

(A) 0.1 to 20% by weight of one or more quaternary ammonium salts represented by the general formula (I)

$$\left[ \begin{array}{c} R_1 \quad R_3 \\ \diagdown \diagup \\ N \\ \diagup \diagdown \\ R_2 \quad R_4 \end{array} \right]^+ X^- \quad \text{(I)}$$

where one or two of $R_1$, $R_2$, $R_3$ and $R_4$ are each a long chain alkyl group having 8 to 20 carbon atoms or a long hydroxyalkyl group having 8 to 20 carbon atoms and the rest of them are each an alkyl group having 1 to 3 carbon atoms, a hydroxyalkyl group having 1 to 3 carbon atoms, a benzyl group or a polyoxyethylene group consisting of a total of not more than 10 molar monomer units; and X is a halogen atom or an alkylsulfuric group having 1 or 2 carbon atoms, (B) 0.1 to 20% by weight of a silicone derivative, and (C) 0.1 to 30% by weight of a polyethylene glycol.

DETAILED DESCRIPTION OF THE PREFERRED EMBODIMENTS

The quaternary ammonium salts of component (A) of the present invention may preferably be, e.g., distearyldimethyl ammonium chloride, stearyltrimethyl ammonium methosulfate, N-stearyl-N,N,N-tri(polyoxyethylene)ammonium chloride (a total of 3 molar monomer units), cethyltriethyl ammonium bromide, and stearyldimethyl ammonium chloride.

The silicone derivative of component (B) may, for example, be as follows:

(1) a dimethylpolysiloxane represented by the following formula (II), $$(CH_3)_3SiO[(CH_3)_2SiO]_{x_1}Si(CH_3)_3 \quad \text{(II)}$$

(where, $x_1$ is an integer of 3 to 650), (2) a methylphenyl polysiloxane represented by either formula (III) or formula (IV), $$(CH_3)_3SiO \left( \begin{array}{c} C_6H_6 \\ \diagdown \\ SiO \\ \diagup \\ CH_3 \end{array} \right)_{x_2} Si(CH_3)_3 \quad \text{(III)}$$

$$(CH_3)_3SiO[(CH_3)_2SiO]_{x_3}[(C_6H_5)_2SiO]_{y_3}Si(CH_3)_3 \quad \text{(IV)}$$

(where $x_2$ is an integer of 1 to 500, and the total of $x_3$ and $y_3$ is an integer of 1 to 500), (3) a polyether modified silicone oil represented by the following formula (V), $$(CH_3)_3SiO[(CH_3)_2SiO]_{x_4}(CH_3SiO)_{y_4}Si(CH_3)_3 \quad \text{(V)}$$
$$\phantom{(CH_3)_3SiO[(CH_3)_2SiO]_{x_4}(}\vert$$
$$\phantom{(CH_3)_3SiO[(CH_3)_2SiO]_{x_4}}(CH_2)_3$$
$$\phantom{(CH_3)_3SiO[(CH_3)_2SiO]_{x_4}(}\vert$$
$$\phantom{(CH_3)_3SiO[(CH_3)}(OC_2H_4)_{m_1}(OC_3H_6)_{n_1}R_5$$

(where $R_5$ is an alkyl group having 1 to 12 carbon atoms, an alkoxy group having 1 to 6 carbon atoms or a hydroxyl group, $x_4$ is an integer of 1 to 100, preferably 20 to 30, $y_4$ is an integer of 1 to 20, preferably 2 to 10, and $n_1$ is an integer of 0 to 50, preferably 20 to 30), (4) an epoxy modified silicone oil represented by the following formula (VI), $$(CH_3)_3SiO[(CH_3)_2SiO]_{x_5}[CH_3SiO]_{y_5}Si(CH_3)_3 \quad (VI)$$

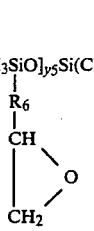

where $R_6$ is an alkylene group having 1 to 3 carbon atoms, $x_5$ is an integer of 1 to 500, preferably 1 to 250, and $y_5$ is an integer of 1 to 50, preferably 1 to 30, (5) a fluorine modified silicone oil represented by the following formula (VII), $$(CH_3)_3SiO(CH_3SiO)_{x_4}Si(CH_3)_3 \quad (VII)$$
$$\underset{CF_3}{\underset{|}{\underset{(CH_2)_2}{|}}}$$

where $x_6$ is an integer of 1 to 400, preferably 1 to 250, (6) an alcohol modified silicone oil represented by the following formula (VIII) or (IX), $$HO(CH_2).R_7[(CH_3)_2SiO]_{x_7}(CH_3)_2SiR_7-CH_2OH \quad (VIII)$$

$$(CH_3)_3SiO[(CH_3)_2SiO]_{x_7}(CH_3SiO)_{y_7}Si(CH_3)_3 \quad (IX)$$
$$\underset{CH_3}{\underset{|}{\underset{CHOH}{\underset{|}{R_7}}}}$$

where $R_7$ is nil or an alkylene group having 1 to 4 carbon atoms, each of $x_7$ and $y_7$ is an integer of 1 to 500, preferably 1 to 200, or (7) an alkyl modified silicone oil represented by the following formula (X) or (XI), $$(CH_3)_3SiO(CH_3SiO)_{x_7}(CH_3SiO)_{y_7}Si(CH_3)_3 \quad (X)$$

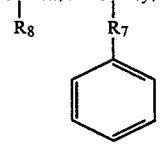

$$(CH_3)_3SiO[(CH_3)_2SiO]_{x_7}(CH_3SiO)_{y_7}Si(CH_3)_3 \quad (XI)$$

where $R_8$ is an alkyl group having 2 to 18 carbon atoms, $R_9$ is an alkyl group having 10 to 16 carbon atoms, and $R_7$, $x_7$ and $y_7$ have the above mentioned meanings.

These silicone derivatives (1) and (7) may be used alone or in combination as a mixture of two or more. Among these, polyether modified silicone oil, dimethylpolysiloxane and methylphenyl polysiloxane are preferred as they give a good feeling to the hair after rinsing. Especially, dimethyl polysiloxane is most preferred.

The polyethylene glycol used as component (C) may be the one having an average molecular weight of 200 to 100,000, preferably 600 to 50,000. Especially, the one having an average molecular weight of 6,000 to 20,000 is most preferred. If the average molecular weight of the polyethylene glycol is less than 200, no adequate effectiveness is expected, and if the average molecular weight is more than 100,000, the viscosity of the composition tends to become too high or it is impossible to obtain a homogeneous composition. In either case, the results will be undesirable to the invention.

As water soluble high molecular compounds resembling the polyethylene glycol, there may be mentioned, polyacrylate, polyvinylalcohol, methylated cellulose, etc. However, some of these compounds are not stable in the composition, and hair rinse compositions obtainable with use of these compounds tend to be non-smooth. Thus, none of them are suitable for the present invention.

The above mentioned components (A), (B) and (C) are preferably combined in the following proportions relative to the total weight of the hair rinse composition. The quaternary ammonium salt of component (A) is 0.1 to 20% by weight (hereinafter simply indicated by %), preferably 0.5 to 5%. The silicone derivative of component (B) is 0.1 to 20%, preferably 0.5 to 5%. If the silicone derivative is less than 0.1%, no adequate effect is obtainable, and if it is more than 20% it becomes difficult to maintain the composition in a stabilized condition. The polyethylene glycol of component (C) is 0.1 to 30%, preferably 0.5 to 5.0%. If the amount is less than 0.1% no adequate effect is obtainable, and if it exceeds 30% it is likely to cause gelation. In either case the result is not desirable to the invention.

The hair rinse composition of the present invention is prepared by dissolving these components in water or, if necessary, in an appropriate solvent such as an alcohol, propylene glycol, glycerine, etc. Further, it is desirable to adjust the pH of the solution by using an organic acid such as citric acid or lactic acid, an inorganic acid such as phosphoric acid or hydrochloric acid, an inorganic alkali such as sodium hydroxide, or an organic alkali such as triethanolamine, in order that a pH-adjusted 5% solution has a pH of 3 to 8 similar to that of an ordinary hair rinse composition.

Further, it is possible to add, as the case requires, fats and oils such as a fatty acid higher alcohol, wool fat, wax, an ester, a liquid paraffin, a higher fatty acid, a germicide, a perfume, etc., to the hair rinse composition of the present invention.

Now, the invention will be described with reference to working examples. However, it should be understood that the invention is not restricted to these examples.

EXAMPLES

EXAMPLE 1

The effectiveness of the silicone derivative and polyethylene glycol combined with the hair rinse composition containing the quaternary ammonium salt, was assessed by measuring the combining force required for combining wet and dry hairs. The results are shown in Table 1.

Hair rinse composition:
1.0% of distearyldimethyl ammonium chloride,
2.0% of a silicone derivative,
2.0% of a polyethylene glycol, and
95% of water.

Measurement of the combining force:
20 g of hair of a Japanese woman having had no hair treatment such as cold permanent-wave set treatment or bleaching treatment, were tied up in a bundle. The hair bundle was immersed at 40° C. in 500 ml of water with 10 g of the hair rinse composition dissolved therein, for 30 seconds, then rinsed with running water for 30 seconds and dried by towelling. The combining loads were measured at 20° C. by strain gauge with respect to both the half-dried hair bundle after the towel drying (wet condition: it contains a moisture of about 0.7 g per gram of hair) and the hair bundle after drying for about 5 minutes with use of a hair drier (dried condition: it contains a moisture of about 0.1 g per gram of hair). The measurement was repeated 20 times, and an average of the measured values was regarded as the combining force.

TABLE I

Conditions of hair at the time of measurement (Unit; g)

| Silicone derivative | Wet condition | | | Dried condition | | |
|---|---|---|---|---|---|---|
| | | Polyethylene glycol | | | Polyethylene glycol | |
| | | PEG | | | PEG | |
| | PEG Nil | Molecular weight 6,000 | Molecular weight 20,000 | PEG Nil | Molecular weight 6,000 | Molecular weight 20,000 |
| Nil | 423 | 323 | 248 | 321 | 254 | 236 |
| Dimethyl polysiloxane | 350 | 296 | 240 | 191 | 177 | 153 |
| Fluorine modified silicone oil | 310 | 249 | 221 | 170 | 142 | 113 |
| Polyether modified silicone oil | 345 | 267 | 233 | 223 | 198 | 170 |
| Epoxy modified silicone oil | 307 | 277 | 201 | 163 | 133 | 115 |
| Alcohol modified silicone oil | 313 | 251 | 222 | 177 | 151 | 145 |
| Alkyl modified silicone oil | 325 | 277 | 236 | 199 | 188 | 172 |

In Table 1, the silicone derivatives are as follows:
Dimethyl polysiloxane: Viscosity: 100,000 centi-stokes.
Fluorine modified silicone oil: In the formula (VII), $x_6$ is 200.
Polyether modified silicone oil: In the formula (V), $x_4$ is 50, $y_4$ is 10, and $m_1$ and $n_1$ are each 20.
Epoxy modified silicone oil: In the formula (VI), $x_5$ is 100, $y_5$ is 10 and $R_6$ is methylene.
Alcohol modified silicone oil: In the formula (VIII), $x_7$ is 100.
Alkyl modified silicone oil: In the formula (XI), $x_7$ is 100 and $y_7$ is 50.

EXAMPLE 2

10 g of each of the hair rinse compositions A (control) and B (product of the present invention) presented below, were dissolved in 500 ml of water, and in the solution thus obtained, 2 bundles of hair (length of 20 cm, weight of 20 g; hereinafter referred to as tress) treated with a shampoo available on the market, were immersed for 30 seconds, and then rinsed for 30 seconds with running water. The tress was towelled. The following evaluations were made with respect to the tress which was still wet and the tress which was dried by being left at room temperature for a half day. The results are shown in Table 2.

Preparation of the hair rinse compositions:

| | A | B |
|---|---|---|
| Distearyldimethyl ammonium chloride | 2.0(%) | 2.0(%) |
| Monostearyltrimethyl ammonium chloride | 0.5 | 0.5 |
| Oil component (liquid paraffin) | 1.5 | — |
| Polyethylene glycol (Molecular weight of 6,000) | — | 0.5 |
| Silicone derivative* | — | 1.0 |
| Water | 96 | 96 |
| pH (5% aqueous solution) | 5.0 | 5.0 |

*The silicone derivative used was the same as used in Example 1.

Method of evaluation:

A panel of 10 women evaluated the feeling by touching the tresses treated with compositions A and B, and an average of the evaluations of the 10 women was regarded as the feeling evaluation.

| Rating: | Softness and flexibility | Stickiness and non-smoothness |
|---|---|---|
| 10 | very soft and flexible | very sticky (non-smooth) |
| 9 | | |
| 8 | Fairly soft and flexible | Fairly sticky and non-smooth |
| 7 | | |
| 6 | Moderately soft and flexible | Moderately sticky and non-smooth |
| 5 | | |
| 4 | Slightly soft and flexible | Slightly sticky and non-smooth |
| 3 | | |
| 2 | Little soft and flexible | Little sticky and non-smooth |
| 1 | | |
| 0 | Absolutely no softness and flexibility | Absolutely no stickiness (non-smoothness) |

TABLE 2

| | | Softness and flexibility | Stickiness and non-smoothness |
|---|---|---|---|
| Products of the present invention (Composition B) | Dimethyl polysiloxane | 7.9 | 2.1 |
| | Polyether modified silicone oil | 8.4 | 1.3 |
| | Alkyl modified silicone oil | 6.4 | 1.2 |
| Comparative product (Composition A) | | 2.7 | 8.9 |

EXAMPLE 3

The following hair rinse compositions were prepared in accordance with the conventional method.

| (1) Cream type hair rinse composition | |
|---|---|
| Dimethyl polysiloxane (Viscosity: 500 centi-stokes) | 2.5% |
| Polyethylene glycol (Molecular weight of 20,000) | 2.0 |
| Distearyldimethyl ammonium chloride | 0.5 |
| Stearyltrimethyl ammonium chloride | 0.5 |
| Stearyl alcohol | 3.0 |
| Glycerine | 5.0 |
| Butyl paraben | 0.05 |
| Perfume | 0.3 |
| Colouring agent | trace |
| Ion-exchanged water | balance |
| (2) Clear type hair rinse composition | |
| Polyether modified silicone oil (Molecular weight of 7,000; 50% modified substance) | 1.0% |
| Polyethylene glycol (Molecular weight of 10,000) | 3.0 |
| Stearyltrimethyl ammonium chloride | 1.0 |
| Ethylene glycol | 7.0 |
| Methyl paraben | 0.05 |
| Perfume | 0.25 |
| Colouring agent | trace |
| Ion-exchanged water | balance |

Each of the above hair rinse compositions exhibited an excellent hair rinse effectiveness.

What is claimed is:

1. A hair rinse composition comsisting essentially of the following three components (A), (B) and (C):

(A) 0.1 to 20 percent by weight of one or more quaternary ammonium salts represented by the general formula (I):

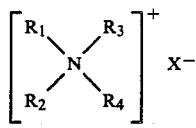

where two of $R_1$, $R_2$, $R_3$ and $R_4$ are each a long chain alkyl group having 8 to 20 carbon atoms and the rest of them are each an alkyl group having 1 to 3 carbon atoms, a benzyl group or a polyoxyethylene group consisting of a total of not more than 10 molar monomer units; and X is a halogen atom;

(B) 0.1 to 20 percent by weight of a dimethylpolysiloxane represented by the following formula:

$$(CH_3)_3SiO[(CH_3)_2SiO]_{x_1}Si(CH_3)_3$$

(where, $x_1$ is an integer of 3 to 650); and (C) 0.1 to 30 percent by weight of polyethylene glycol having an average molecular weight of 200 to 100,000.

* * * * *